(12) United States Patent
Cumberland et al.

(10) Patent No.: US 7,637,271 B1
(45) Date of Patent: Dec. 29, 2009

(54) POLYALUMINUM COMPOSITIONS

(75) Inventors: Scott Cumberland, Pleasanton, CA (US); Maria Ochomogo, Danville, CA (US)

(73) Assignee: The Clorox Company, Oakland, CA (US)

( * ) Notice: Subject to any disclaimer, the term of this patent is extended or adjusted under 35 U.S.C. 154(b) by 0 days.

(21) Appl. No.: 12/261,294

(22) Filed: Oct. 30, 2008

(51) Int. Cl.
*B08B 3/04* (2006.01)
*C11D 1/66* (2006.01)
*C11D 3/02* (2006.01)
*C11D 3/22* (2006.01)
*C11D 3/43* (2006.01)

(52) U.S. Cl. .................. 134/25.2; 134/25.3; 134/39; 134/40; 134/42; 510/238; 510/239; 510/240; 510/248; 510/421; 510/426; 510/432; 510/474; 510/508; 510/532

(58) Field of Classification Search .......... 510/238, 510/239, 240, 248, 421, 426, 432, 474, 508, 510/532; 134/25.2, 39, 25.3, 40, 42
See application file for complete search history.

(56) References Cited

U.S. PATENT DOCUMENTS

| | | |
|---|---|---|
| 4,656,059 A | 4/1987 | Mizuno |
| 5,523,000 A | 6/1996 | Falbaum |
| 5,653,795 A | 8/1997 | Brown |
| 5,741,768 A | 4/1998 | Falbaum |
| 5,750,484 A | 5/1998 | Falbaum |
| 5,824,192 A | 10/1998 | Radu |
| 6,033,525 A | 3/2000 | Moffett |
| 6,248,711 B1 | 6/2001 | Mizuno |
| 6,248,793 B1 | 6/2001 | Severtson |
| 6,699,827 B2 | 3/2004 | Kim |
| 6,958,362 B2 | 10/2005 | Kim |
| 7,157,009 B2 | 1/2007 | Nochols |
| 2002/0188040 A1 | 12/2002 | Chen |
| 2003/0066540 A1 | 4/2003 | Sachdev |
| 2005/0242041 A1 | 11/2005 | Cumberland |

FOREIGN PATENT DOCUMENTS

JP 53-45309 * 4/1978

* cited by examiner

*Primary Examiner*—Brian P Mruk
(74) *Attorney, Agent, or Firm*—Alok Goel

(57) ABSTRACT

A cleaning composition with a limited number of ingredients contains a polyaluminum compound and surfactant. The cleaning composition optionally has an additional amount of fragrance. The cleaning composition optionally has a small amount of solvent. The cleaning composition optionally comprises a comprises a group selected from the group consisting of a dye, a builder, a fatty acid, a colorant, a preservative, a chelating agent, a colloidal silica and mixtures thereof.

31 Claims, No Drawings

POLYALUMINUM COMPOSITIONS

BACKGROUND OF THE INVENTION

1. Field of the Invention

The present invention relates generally to polyaluminum cleaning and laundry compositions. In one embodiment, the present invention relates to polyaluminum cleaning compositions for use on hard surfaces. In one embodiment, the present invention relates to polyaluminum cleaning compositions for use on glass surfaces. In one embodiment, the present invention relates to polyaluminum fabric softeners. In one embodiment, the present invention relates to polyaluminum air/fabric refresher. The invention also relates to cleaning compositions for use with cleaning substrates, cleaning heads, cleaning pads, cleaning sponges and related systems for cleaning hard surfaces.

2. Description of the Related Art

Polyaluminum compounds represent a series of water-soluble, inorganic, polymeric compounds with a high charge density and ranging in aluminum oxide content, degree of polymerization and acid neutralization. Due to their high charge density, these materials have typically been used in the water treatment industry for removal of sediment, heavy metals, natural organic matter and microorganisms. Polyaluminum compounds have also been used in the photography and copying industry for improved retention of ink and toner on paper. Polyaluminum compounds have also been used in the pulp and paper industry for improved processing and increased paper strength. Polyaluminum compounds have also been used in the personal care industry for enhanced wetness and odor control for deodorants and antiperspirants.

However, polyaluminum compounds have not been readily utilized in the cleaning and laundry industry. Addition of polyaluminum compounds to cleaning substrates result in improved release of quaternary ammonium biocides as well as improved dirt removal from a surface and retention on a wipe. In fact, polyaluminum compounds can be used in any application where improved quaternary ammonium release or improved soil removal is desired and obtained from the use of cationic organic polymers or chelating agents such as applications related to cleaning hard surfaces. Polyaluminum compounds may be also be used in air and fabric refresher products to reduce the presence of odors and to prevent dust particles and allergens from being released into the air. Additionally, polyaluminum compounds may bind allergens and immobilize microorganisms thereby reducing the spread of illnesses or diseases and consequently, improving the quality of the air being breathed. Since polyaluminum compounds do not contain organic groups (i.e. amines), polyaluminum compounds do not degrade upon heating or upon exposure to UV light and therefore do not discolor fabrics. Therefore, there are some tangible benefits to using polyaluminum compounds in the cleaning and laundry industry.

Polyaluminum compounds are considered natural ingredients because they are derived from mineral resources as opposed to organic materials derived from petrochemical resources. Because of a desire to use renewable resources, natural based cleaners and laundry products are gaining increasing interest over traditional synthetic products. Most of the cleaners in the market contain only some natural ingredients. One difficulty in formulating natural based cleaners is achieving acceptable consumer performance with a limited number of natural components compared to highly developed formulations using synthetic surfactants and solvents.

Typical cleaning formulations require multiple surfactants, solvents, and builder combinations to achieve adequate consumer performance. For example, U.S. Pat. No. 5,025,069 to Deguchi et al. discloses alkyl glycoside detergent systems with anionic, amphoteric and nonionic surfactant ingredients. U.S. Pat. No. 7,182,950 to Garti et al. discloses nano-sized concentrates with examples using Tween® surfactants. U.S. Pat. No. 6,831,050 to Murch et al. discloses toxicologically acceptable cleaners containing oleic acid and citric acid. U.S. Pat. No. 6,302,969 to Moster et al. discloses natural cleaners containing anionic surfactants. U.S. Pat. No. 6,420,326 to Maile et al. discloses glass cleaners with ethanol, glycol ethers, and anionic surfactants.

Prior art compositions do not combine effective cleaning with a minimum number of ingredients, especially with natural ingredients. It is therefore an object of the present invention to provide a cleaning composition that overcomes the disadvantages and shortcomings associated with prior art cleaning compositions.

SUMMARY OF THE INVENTION

In accordance with the above objects and those that will be mentioned and will become apparent below, one aspect of the present invention comprises a stable, aqueous cleaning composition comprising: a) 0.01-20.0% polyaluminum compound and b) 0.1-5.0% of a surfactant selected from the group consisting of nonionic, anionic, cationic, amphoteric, zwitterionic and mixtures thereof.

In accordance with the above objects and those that will be mentioned and will become apparent below, another aspect of the present invention comprises a natural, hard surface cleaning composition comprising a) 0.01-20.0% polyaluminum chloride and b) 0.1-5.0% of an alkyl polyglucoside.

In accordance with the above objects and those that will be mentioned and will become apparent below, another aspect of the present invention comprises a method for cleaning a surface using natural ingredients comprising: contacting the surface with a composition, wherein the composition comprises a) 0.01-20.0% polyaluminum chloride and b) 0.1-5.0% of an alkyl polyglucoside.

Further features and advantages of the present invention will become apparent to those of ordinary skill in the art in view of the detailed description of preferred embodiments below, when considered together with the attached claims.

DETAILED DESCRIPTION OF THE INVENTION

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural references unless the content clearly dictates otherwise. Thus, for example, reference to a "surfactant" includes two or more such surfactants.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentage ("%'s") are in weight percent (based on 100% active) of the cleaning composition alone, not accounting for the substrate weight. Each of the noted cleaner composition components and substrates is discussed in detail below.

The term "cleaning composition", as used herein, is meant to mean and include a cleaning formulation having at least one surfactant.

The term "surfactant", as used herein, is meant to mean and include a substance or compound that reduces surface tension when dissolved in water or water solutions, or that reduces interfacial tension between two liquids, or between a liquid and a solid. The term "surfactant" thus includes, but is not limited to, anionic, cationic, nonionic, zwitterionic and/or amphoteric agents.

The term "consisting essentially of" as used herein, limits the scope of a claim to the specified materials or steps "and those that do not materially affect the basic and novel characteristic(s)" of the claimed invention. In re Herz, 537 F.2d 549, 551-52, 190 USPQ 461, 463 (CCPA 1976) (emphasis in original). See MPEP 2111.03 For the purposes of searching for and applying prior art under 35 U.S.C. 102 and 103, absent a clear indication in the specification or claims of what the basic and novel characteristics actually are, "consisting essentially of" will be construed as equivalent to "comprising." See, e.g., PPG, 156 F.3d at 1355, 48 USPQ2d at 1355. See MPEP 2111.03

The term "natural" as used herein is meant to mean at least 95% of the components of the product are derived from plant and mineral based materials. Also, the "natural" product is biodegradable. Additionally, the "natural" product is minimally toxic to humans and has a LD50>5000 mg/kg. The "natural" product does not contain of any of the following: non-plant based ethoxylated surfactants, linear alkylbenzene sulfonates ("LAS"), ether sulfates surfactants or nonylphenol ethoxylate (NPE).

The term "ecofriendly" as used herein is meant to mean at least 99% of the components of the product are derived from plant and mineral based materials. Also, the "ecofriendly" product is biodegradable. Additionally, the "ecofriendly" product is minimally toxic to humans and has a LD50>5000 mg/kg. The "ecofriendly" product does not contain of any of the following: non-plant based ethoxylated surfactants, linear alkylbenzene sulfonates ("LAS"), ether sulfates surfactants or nonylphenol ethoxylate (NPE).

The term "biodegradable" as used herein is meant to mean microbial degradation of carbon containing materials. The "biodegradable" material must be tested under a recognized protocol and with tested methods of established regulatory bodies such as: EPA, EPA-TSCA, OECD, MITI or other similar or equivalent organizations in the US or internationally. Suitable non-limiting examples of test methods for biodegradation include: OECD methods in the 301-305 series. Generally, all "biodegradable" material must meet the following limitations:

a) removal of dissolved organic carbon >70%
b) biological oxygen demand (BOD) >60%
c) % of BOD of theoretical oxygen demand >60%
d) % $CO_2$ evolution of theoretical >60%

Surfactants

The cleaning composition may contain one or more surfactants selected from nonionic, anionic, cationic, ampholytic, amphoteric and zwitterionic surfactants and mixtures thereof. A typical listing of anionic, ampholytic, and zwitterionic classes, and species of these surfactants, is given in U.S. Pat. No. 3,929,678 to Laughlin and Heuring. A list of suitable cationic surfactants is given in U.S. Pat. No. 4,259,217 to Murphy. The surfactants may be present at a level of from about 0.1% to about 90%, or from about 0.1% to about 70%, or from about 0.1% to about 50%, or from about 0.1% to about 25%, or from about 0.1% to about 10%, or from about 0.1% to about 8.0%, or from about 0.1% to about 7.0%, or from about 0.1% to about 6.0%, or from about 0.1% to about 5.0%, or from about 0.1% to about 4.0%, or from about 0.1% to about 3.0% or from about 0.1% to about 2.0% or from about 0.1% to about 1.0%.

The cleaning composition may comprise an anionic surfactant. Essentially any anionic surfactants useful for detersive purposes can be used in the cleaning composition. These can include salts (including, for example, sodium, potassium, ammonium, and substituted ammonium salts such as mono-, di- and tri-ethanolamine salts) of the anionic sulfate, sulfonate, carboxylate and sarcosinate surfactants. Anionic surfactants may comprise a sulfonate or a sulfate surfactant. Anionic surfactants may comprise an alkyl sulfate, a linear or branched alkyl benzene sulfonate, or an alkyldiphenyloxide disulfonate, as described herein.

Other anionic surfactants include the isethionates such as the acyl isethionates, N-acyl taurates, fatty acid amides of methyl tauride, alkyl succinates and sulfosuccinates, monoesters of sulfosuccinate (for instance, saturated and unsaturated C12-C18 monoesters) diesters of sulfosuccinate (for instance saturated and unsaturated C6-C14 diesters), N-acyl sarcosinates. Resin acids and hydrogenated resin acids are also suitable, such as rosin, hydrogenated rosin, and resin acids and hydrogenated resin acids present in or derived from tallow oil. Anionic sulfate surfactants suitable for use herein include the linear and branched primary and secondary alkyl sulfates, alkyl ethoxysulfates, fatty oleoyl glycerol sulfates, alkyl phenol ethylene oxide ether sulfates, the C5-C17acyl-N—(C1-C4 alkyl) and —N—(C1-C2 hydroxyalkyl) glucamine sulfates, and sulfates of alkylpolysaccharides such as the sulfates of alkylpolyglucoside (the nonionic nonsulfated compounds being described herein). Alkyl sulfate surfactants may be selected from the linear and branched primary C10-C18 alkyl sulfates, the C11-C15 branched chain alkyl sulfates, or the C12-C14 linear chain alkyl sulfates.

Alkyl ethoxysulfate surfactants may be selected from the group consisting of the C10-C18 alkyl sulfates, which have been ethoxylated with from 0.5 to 20 moles of ethylene oxide per molecule. The alkyl ethoxysulfate surfactant may be a C11-C18, or a C11-C15 alkyl sulfate which has been ethoxylated with from 0.5 to 7, or from 1 to 5, moles of ethylene oxide per molecule. One aspect of the invention employs mixtures of the alkyl sulfate and/or sulfonate and alkyl ethoxysulfate surfactants. Such mixtures have been disclosed in PCT Patent Application No. WO 93/18124.

Anionic sulfonate surfactants suitable for use herein include the salts of C5-C20 linear alkylbenzene sulfonates, alkyl ester sulfonates, C6-C22 primary or secondary alkane sulfonates, C6-C24 olefin sulfonates, sulfonated polycarboxylic acids, alkyl glycerol sulfonates, fatty acyl glycerol sulfonates, fatty oleyl glycerol sulfonates, and any mixtures thereof. Suitable anionic carboxylate surfactants include the alkyl ethoxy carboxylates, the alkyl polyethoxy polycarboxylate surfactants and the soaps ('alkyl carboxyls'), especially certain secondary soaps as described herein. Suitable alkyl ethoxy carboxylates include those with the formula $RO(CH_2CH_2O)_xCH_2COO^-M^+$ wherein R is a C6 to C18 alkyl group, x ranges from 0 to 10, and the ethoxylate distribution is such that, on a weight basis, the amount of material where x is 0 is less than 20% and M is a cation. Suitable alkyl polyethoxypolycarboxylate surfactants include those having the formula $RO—(CHR^1CHR^2—O)_x—R^3$ wherein R is a C6 to C18 alkyl group, x is from 1 to 25, $R^1$ and $R^2$ are selected from the group consisting of hydrogen, methyl acid radical, succinic acid radical, hydroxysuccinic acid radical, and mixtures thereof, and $R^3$ is selected from the group consisting of hydrogen, substituted or unsubstituted hydrocarbon having between 1 and 8 carbon atoms, and mixtures thereof.

Suitable soap surfactants include the secondary soap surfactants, which contain a carboxyl unit connected to a secondary carbon. Suitable secondary soap surfactants for use herein are water-soluble members selected from the group consisting of the water-soluble salts of 2-methyl-1-undecanoic acid, 2-ethyl-1-decanoic acid, 2-propyl-1-nonanoic acid, 2-butyl-1-octanoic acid and 2-pentyl-1-heptanoic acid. Certain soaps may also be included as suds suppressors.

Other suitable anionic surfactants are the alkali metal sarcosinates of formula $R—CON(R^1)CH—)COOM$, wherein R is a C5-C17 linear or branched alkyl or alkenyl group, $R^1$ is a C1-C4 alkyl group and M is an alkali metal ion. Examples are the myristyl and oleoyl methyl sarcosinates in the form of their sodium salts.

Other suitable surfactants include fatty acid sarcosinates which are mild, biodegradable anionic surfactants derived from fatty acids and sarcosine (amino acid). Sarcosine is the N-methyl derivative of glycine. Sarcosine is a natural amino acid found in muscles and other tissues. Sarcosine is found naturally as an intermediate in the metabolism of choline to glycine. In a preferred embodiment, the sarcosines are acyl sarcosines. Examples of acyl sarcosines include, but are not limited to, cocoyl sarcosine, lauroyl sarcosine, myristoyl sarcosine, oleoyl sarcosine, stearoyl sarcosine which are modified fatty acids. The salts of acyl sarcosines are referred to acyl sarcosinates. Acyl sarcosinates useful herein include, for example, those having a formula:

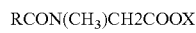

$RCON(CH_3)CH2COOX$ wherein R is an alkyl or alkenyl having from 8 to 22 carbon atoms, preferably from 12 to 18 carbon atoms, more preferably from 12 to 14 carbon atoms; and X is a sodium, potassium, ammonium, or triethanolamine.

Examples of acyl sarcosinates that can be used with the present invention include, but not limited to, sodium coccyl sarcosinate, sodium lauroyl sarcosinate and sodium myristoyl sarcosinate, sodium oleoyl sarcosinate, sodium stearoyl sarcosinate, ammonium coccyl sarcosinate, ammonium lauroyl sarcosinate and ammonium myristoyl sarcosinate, ammonium oleoyl sarcosinate and ammonium stearoyl sarcosinate. Commercially available preferred acyl sarcosinates include, but are not limited to, for example, sodium lauroyl sarcosinate having the tradename Hamposyl® L30 which is available from Hampshire Chemicals, and sodium cocoyl sarcosinate having the tradename Hamposyl® C30 which is available from Hampshire Chemicals.

Other suitable surfactants include fatty alcohol sulfate which has a higher alcohol or alkyl group is normally in the range of 10 to 18 carbon atoms. The cation will almost invariably be sodium or will include sodium, although other cations, such as triethanolamine, potassium, ammonium, magnesium and calcium. Preferred fatty alcohol sulfates are those wherein the fatty alcohol is essentially saturated and is of carbon content(s) within the 10 to 18 carbon atoms range, preferably 10 or 12 to 14 or 16 carbon atoms, such as 12 to 16, or that is derived from coconut oil (coco), palm oil, or palm kernel oil. Lauryl sulfates, and particularly, sodium lauryl sulfate, are preferred primary detergents but such designation also may apply to such detergents wherein the carbon chain length of the alcohol is not limited to 12 carbon atoms, but is primarily (over 50% and normally over 70 or 75%) of 12 to 14 carbon atoms. Such materials may be obtained from natural sources, such as coconut oil and palm kernel oil. In one embodiment, the fatty alcohol sulfate is a C12-C18 fatty alcohol sulfate. In another embodiment, the fatty alcohol sulfate is a C12-C16 fatty alcohol sulfate. In another embodiment, the fatty alcohol sulfate is a C12-C14 fatty alcohol sulfate. In another embodiment, the fatty alcohol is a C12 fatty alcohol sulfate. In another embodiment, the fatty alcohol sulfate is sodium lauryl sulfate. In a specific embodiment, the fatty alcohol sulfate is a sodium coco fatty alcohol sulfate.

Suitable amphoteric surfactants for use herein include the amine oxide surfactants and the alkyl amphocarboxylic acids. Suitable amine oxides include those compounds having the formula $R^3(OR^4)_xNO(R^5)_2$ wherein $R^3$ is selected from an alkyl, hydroxyalkyl, acylamidopropyl and alkylphenyl group, or mixtures thereof, containing from 8 to 26 carbon atoms; $R^4$ is an alkylene or hydroxyalkylene group containing from 2 to 3 carbon atoms, or mixtures thereof, x is from 0 to 5, preferably from 0 to 3; and each $R^5$ is an alkyl or hydroxyalkyl group containing from 1 to 3, or a polyethylene oxide group containing from 1 to 3 ethylene oxide groups. Suitable amine oxides are C10-C18 alkyl dimethylamine oxide, and C10-18 acylamido alkyl dimethylamine oxide. A suitable example of an alkyl amphodicarboxylic acid is Miranol™ C2M Conc. manufactured by Miranol, Inc., Dayton, N.J.

Zwitterionic surfactants can also be incorporated into the cleaning compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. Betaine and sultaine surfactants are exemplary zwittenionic surfactants for use herein.

Suitable betaines are those compounds having the formula $R(R^1)_2N^+R^2COO^-$ wherein R is a C6-C18 hydrocarbyl group, each $R^1$ is typically C1-C3 alkyl, and $R^2$ is a C1-C5 hydrocarbyl group. Suitable betaines are C12-18 dimethylammonio hexanoate and the C10-18 acylamidopropane (or ethane) dimethyl (or diethyl) betaines. Complex betaine surfactants are also suitable for use herein.

Suitable cationic surfactants to be used herein include the quaternary ammonium surfactants. The quaternary ammonium surfactant may be a mono C6-C16, or a C6-C10 N-alkyl or alkenyl ammonium surfactant wherein the remaining N positions are substituted by methyl, hydroxyethyl or hydroxypropyl groups. Suitable are also the mono-alkoxylated and bis-alkoxylated amine surfactants. Additional suitable cationic surfactants include coco fatty acid diethanolamine, hydrogenated palm tea ester quat, and cationic ethoxylate fatty acids.

Another suitable group of cationic surfactants, which can be used in the cleaning compositions, are cationic ester surfactants. The cationic ester surfactant is a compound having surfactant properties comprising at least one ester (i.e. —COO—) linkage and at least one cationically charged group. Suitable cationic ester surfactants, including choline ester surfactants, have for example been disclosed in U.S. Pat.

Nos. 4,228,042, 4,239,660 and 4,260,529. The ester linkage and cationically charged group may be separated from each other in the surfactant molecule by a spacer group consisting of a chain comprising at least three atoms (i.e. of three atoms chain length), or from three to eight atoms, or from three to five atoms, or three atoms. The atoms forming the spacer group chain are selected from the group consisting of carbon, nitrogen and oxygen atoms and any mixtures thereof, with the proviso that any nitrogen or oxygen atom in said chain connects only with carbon atoms in the chain. Thus spacer groups having, for example, —O—O— (i.e. peroxide), —N—N—, and —N—O— linkages are excluded, whilst spacer groups having, for example —$CH_2$—O—, $CH_2$— and —$CH_2$—NH—$CH_2$— linkages are included. The spacer group chain may comprise only carbon atoms, or the chain is a hydrocarbyl chain.

The cleaning composition may comprise cationic mono-alkoxylated amine surfactants, for instance, of the general formula: $R^1R^2R^3N^+ApR^4X^-$ wherein $R^1$ is an alkyl or alkenyl moiety containing from about 6 to about 18 carbon atoms, or from 6 to about 16 carbon atoms, or from about 6 to about 14 carbon atoms; $R^2$ and $R^3$ are each independently alkyl groups containing from one to about three carbon atoms, for instance, methyl, for instance, both $R^2$ and $R^3$ are methyl groups; $R^4$ is selected from hydrogen, methyl and ethyl; $X^-$ is an anion such as chloride, bromide, methylsulfate, sulfate, or the like, to provide electrical neutrality; A is a alkoxy group, especially a ethoxy, propoxy or butoxy group; and p is from 0 to about 30, or from 2 to about 15, or from 2 to about 8. The $ApR^4$ group in the formula may have p=1 and is a hydroxyalkyl group, having no greater than 6 carbon atoms whereby the —OH group is separated from the quaternary ammonium nitrogen atom by no more than 3 carbon atoms. Suitable $ApR^4$ groups are —$CH_2CH_2$—OH, —$CH_2CH_2CH_2$—OH, —$CH_2CH(CH_3)$—OH and —$CH(CH_3)CH_2$—OH. Suitable $R^1$ groups are linear alkyl groups, for instance, linear $R^1$ groups having from 8 to 14 carbon atoms.

Suitable cationic mono-alkoxylated amine surfactants for use herein are of the formula $R^1(CH_3)(CH_3)N^+(CH_2CH_2O)_{2-5}HX^-$ wherein $R^1$ is C10-C18 hydrocarbyl and mixtures thereof, especially C10-C14 alkyl, or C10 and C12 alkyl, and X is any convenient anion to provide charge balance, for instance, chloride or bromide.

As noted, compounds of the foregoing type include those wherein the ethoxy ($CH_2CH_2O$) units (EO) are replaced by butoxy, isopropoxy [$CH(CH_3)CH_2O$] and [$CH_2CH(CH_3)O$] units (i-Pr) or n-propoxy units (Pr), or mixtures of EO and/or Pr and/or i-Pr units.

The cationic bis-alkoxylated amine surfactant may have the general formula: $R^1R^2N^+ApR^3A'qR^4X^-$ wherein $R^1$ is an alkyl or alkenyl moiety containing from about 8 to about 18 carbon atoms, or from 10 to about 16 carbon atoms, or from about 10 to about 14 carbon atoms; $R^2$ is an alkyl group containing from one to three carbon atoms, for instance, methyl; $R^3$ and $R^4$ can vary independently and are selected from hydrogen, methyl and ethyl, $X^-$ is an anion such as chloride, bromide, methylsulfate, sulfate, or the like, sufficient to provide electrical neutrality. A and A' can vary independently and are each selected from C1-C4 alkoxy, for instance, ethoxy, (i.e., —$CH_2CH_2O$—), propoxy, butoxy and mixtures thereof, p is from 1 to about 30, or from 1 to about 4 and q is from 1 to about 30, or from 1 to about 4, or both p and q are 1.

Suitable cationic bis-alkoxylated amine surfactants for use herein are of the formula $R^1CH_3N^+(CH_2CH_2OH)(CH_2CH_2OH) X^-$, wherein $R^1$ is C10-C18 hydrocarbyl and mixtures thereof, or C10, C12, C14 alkyl and mixtures thereof, $X^-$ is any convenient anion to provide charge balance, for example, chloride. With reference to the general cationic bis-alkoxylated amine structure noted above, since in one example compound $R^1$ is derived from (coconut) C12-C14 alkyl fraction fatty acids, $R^2$ is methyl and $ApR^3$ and $A'qR^4$ are each monoethoxy.

Other cationic bis-alkoxylated amine surfactants useful herein include compounds of the formula: $R^1R^2N^+$—$(CH_2CH_2O)_pH$—$(CH_2CH_2O)_qHX^-$ wherein $R^1$ is C10-C18 hydrocarbyl, or C10-C14 alkyl, independently p is 1 to about 3 and q is 1 to about 3, $R^2$ is C1-C3 alkyl, for example, methyl, and $X^-$ is an anion, for example, chloride or bromide.

Other compounds of the foregoing type include those wherein the ethoxy ($CH_2CH_2O$) units (EO) are replaced by butoxy (Bu) isopropoxy [$CH(CH_3)CH_2O$] and [$CH_2CH(CH_3)O$] units (i-Pr) or n-propoxy units (Pr), or mixtures of EO and/or Pr and/or i-Pr units.

The inventive compositions may include at least one fluorosurfactant selected from nonionic fluorosurfactants, cationic fluorosurfactants, and mixtures thereof which are soluble or dispersible in the aqueous compositions being taught herein, sometimes compositions which do not include further detersive surfactants, or further organic solvents, or both. Suitable nonionic fluorosurfactant compounds are found among the materials presently commercially marketed under the tradename Fluorad® (ex. 3M Corp.) Exemplary fluorosurfactants include those sold as Fluorad® FC-740, generally described to be fluorinated alkyl esters; Fluorad® FC-430, generally described to be fluorinated alkyl esters; Fluorad® FC-431, generally described to be fluorinated alkyl esters; and, Fluorad® FC-170-C, which is generally described as being fluorinated alkyl polyoxyethylene ethanols.

An example of a suitable cationic fluorosurfactant compound has the following structure: $C_nF_{2n+1}SO_2NHC_3H_6N^+(CH_3)_3I^-$ where n~8. This cationic fluorosurfactant is available under the tradename Fluorad® FC-135 from 3M. Another example of a suitable cationic fluorosurfactant is $F_3$—$(CF_2)_n$—$(CH_2)_mSCH_2CHOH$—$CH_2$—$N^+R_1R_2R_3$ $Cl^-$ wherein: n is 5-9 and m is 2, and $R_1$, $R_2$ and $R_3$ are —$CH_3$. This cationic fluorosurfactant is available under the tradename ZONYL® FSD (available from DuPont, described as 2-hydroxy-3-((gamma-omega-perfluoro-$C_{6-20}$-alkyl)thio)-N,N,N-trimethyl-1-propyl ammonium chloride). Other cationic fluorosurfactants suitable for use in the present invention are also described in EP 866,115 to Leach and Niwata. The fluorosurfactant selected from the group of nonionic fluorosurfactant, cationic fluorosurfactant, and mixtures thereof may be present in amounts of from 0.001 to 5% wt., preferably from 0.01 to 1% wt., and more preferably from 0.01 to 0.5% wt.

The cleaning composition may comprise a nonionic surfactant. Essentially any alkoxylated nonionic surfactants are suitable herein, for instance, ethoxylated and propoxylated nonionic surfactants. Alkoxylated surfactants can be selected from the classes of the nonionic condensates of alkyl phenols, nonionic ethoxylated alcohols, nonionic ethoxylated/propoxylated fatty alcohols, nonionic ethoxylate/propoxylate condensates with propylene glycol, and the nonionic ethoxylate condensation products with propylene oxide/ethylene diamine adducts.

The condensation products of aliphatic alcohols with from 1 to 25 moles of alkylene oxide, particularly ethylene oxide and/or propylene oxide, are suitable for use herein. The alkyl chain of the aliphatic alcohol can either be straight or branched, primary or secondary, and generally contains from 6 to 22 carbon atoms. Also suitable are the condensation products of alcohols having an alkyl group containing from 8 to 20 carbon atoms with from 2 to 10 moles of ethylene oxide per mole of alcohol.

Polyhydroxy fatty acid amides suitable for use herein are those having the structural formula $R^2CONR^1Z$ wherein: $R^1$ is H, C1-C4 hydrocarbyl, 2-hydroxyethyl, 2-hydroxypropyl, ethoxy, propoxy, or a mixture thereof, for instance, C1-C4 alkyl, or C1 or C2 alkyl; and $R^2$ is a C5-C31 hydrocarbyl, for instance, straight-chain C5-C19 alkyl or alkenyl, or straight-chain C9-C17 alkyl or alkenyl, or straight-chain C11-C17 alkyl or alkenyl, or mixture thereof, and Z is a polyhydroxyhydrocarbyl having a linear hydrocarbyl chain with at least 3 hydroxyls directly connected to the chain, or an alkoxylated derivative (for example, ethoxylated or propoxylated) thereof. Z may be derived from a reducing sugar in a reductive amination reaction, for example, Z is a glycityl.

Suitable fatty acid amide surfactants include those having the formula: $R^1CON(R^2)_2$ wherein $R^1$ is an alkyl group containing from 7 to 21, or from 9 to 17 carbon atoms and each $R^2$ is selected from the group consisting of hydrogen, C1-C4 alkyl, C1-C4 hydroxyalkyl, and —$(C_2H_4O)_xH$, where x is in the range of from 1 to 3.

Suitable alkylpolysaccharides for use herein are disclosed in U.S. Pat. No. 4,565,647 to Llenado, having a hydrophobic group containing from 6 to 30 carbon atoms and a polysaccharide, e.g., a polyglycoside, hydrophilic group containing from 1.3 to 10 saccharide units. Alkylpolyglycosides may have the formula: $R^2O(C_nH_{2n}O)_t(glycosyl)_x$ wherein $R^2$ is selected from the group consisting of alkyl, alkylphenyl, hydroxyalkyl, hydroxyalkylphenyl, and mixtures thereof in which the alkyl groups contain from 10 to 18 carbon atoms; n is 2 or 3; t is from 0 to 10, and x is from 1.3 to 8. The glycosyl may be derived from glucose.

Other suitable nonionic surfactants are food safe nonionic surfactants. Examples of food safe nonionic surfactants are sucrose esters, such as sucrose cocoate available from Croda, and sorbitan esters, such as polyoxyethylene(20) sorbitan monooleate from J. T. Baker and polyoxyethylene(20) sorbitan monolaurate from Uniquema. Other examples of food safe nonionic surfactants are given in Generally Recognized As Safe (GRAS) lists, as described below.

In a preferred embodiment, the compositions may specifically contain alkyl polyglucoside ("APG") surfactant. The cleaning compositions preferably have an absence of other nonionic surfactants, especially synthetic nonionic surfactants, such as ethoxylates. The cleaning compositions preferably have an absence of other surfactants, such as anionic, cationic, and amphoteric surfactants. Suitable alkyl polyglucoside surfactants are the alkylpolysaccharides that are disclosed in U.S. Pat. No. 5,776,872 to Giret et al.; U.S. Pat. No. 5,883,059 to Furman et al.; U.S. Pat. No. 5,883,062 to Addison et al.; and U.S. Pat. No. 5,906,973 to Ouzounis et al., which are all incorporated by reference. Suitable alkyl polyglucosides for use herein are also disclosed in U.S. Pat. No. 4,565,647 to Llenado describing alkylpolyglucosides having a hydrophobic group containing from about 6 to about 30 carbon atoms, or from about 10 to about 16 carbon atoms and polysaccharide, e.g., a polyglycoside, hydrophilic group containing from about 1.3 to about 10, or from about 1.3 to about 3, or from about 1.3 to about 2.7 saccharide units. Optionally, there can be a polyalkyleneoxide chain joining the hydrophobic moiety and the polysaccharide moiety. A suitable alkyleneoxide is ethylene oxide. Typical hydrophobic groups include alkyl groups, either saturated or unsaturated, branched or unbranched containing from about 8 to about 18, or from about 10 to about 16, carbon atoms. Suitably, the alkyl group can contain up to about 3 hydroxy groups and/or the polyalkyleneoxide chain can contain up to about 10, or less than about 5, alkyleneoxide moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses. Suitable mixtures include coconut alkyl, di-, tri-, tetra-, and pentaglucosides and tallow alkyl tetra-, penta-, and hexaglucosides.

Suitable alkylpolyglycosides (or alkylpolyglucosides) have the formula: $R^2O(C_nH_{2n}O)_t(glycosyl)_x$ wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is about 2 or about 3, preferably about 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

A group of alkyl glycoside surfactants suitable for use in the practice of this invention may be represented by formula I below:

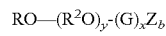

$$RO—(R^2O)_y\text{-}(G)_xZ_b \qquad I$$

wherein R is a monovalent organic radical containing from about 6 to about 30 (preferably from about 8 to about 18) carbon atoms; $R^2$ is a divalent hydrocarbon radical containing from about 2 to about 4 carbon atoms; O is an oxygen atom; y is a number which has an average value from about 0 to about 1 and is preferably 0; G is a moiety derived from a reducing saccharide containing 5 or 6 carbon atoms; and x is a number having an average value from about 1 to 5 (preferably from 1.1 to 2); Z is $O_2M^1$, $O_2CR^3$, $O(CH_2)$, $CO_2M^1$, $OSO_3M^1$, or $O(CH_2)SO_3M^1$; $R^3$ is $(CH_2)CO_2M^1$ or $CH=CHCO_2M^1$; (with the proviso that Z can be $O_2M^1$ only if Z is in place of a primary hydroxyl group in which the primary hydroxyl-bearing carbon atom, —$CH_2OH$, is oxidized to form a —$CO_2M^1$ group); b is a number from 0 to 3x+1 preferably an average of from 0.5 to 2 per glycosal group; p is 1 to 10, $M^1$ is $H^+$ or an organic or inorganic cation, such as, for example, an alkali metal, ammonium, monoethanolamine, or calcium. As defined in Formula I, R is generally the residue of a fatty alcohol having from about 8 to 30 or 8 to 18 carbon atoms. Suitable alkylglycosides include, for example, APG 325® (a $C_9$-$C_{11}$ alkyl polyglycoside available from Cognis Corporation), APG 625® (a $C_{10}$-$C_{16}$ alkyl polyglycoside available from Cognis Corporation), Dow Triton® CG110 (a $C_8$-$C_{10}$ alkyl polyglycoside available from Dow Chemical Company), AG6202® (a $C_8$ alkyl polyglycoside available from Akzo Nobel) Glucopon® 425N (a $C_8$-$C_{16}$ alkyl polyglycoside available from Cognis Corporation), Glucopon® 215 (a $C_8$-$C_{10}$ alkyl polyglycoside available from Cognis Corporation), Glucpon® 225 (a $C_8$-$C_{10}$ alkyl polyglycoside available from Cognis Corporation) and Alkadet 15® (a $C_8$-$C_{10}$ alkyl polyglycoside available from Huntsman Corporation). A $C_8$ to $C_{10}$ alkylpoly-glucoside includes alkylpolyglucosides wherein the alkyl group is substantially C8 alkyl, substantially C10 alkyl, or a mixture of substantially C8 and C10 alkyl. Additionally, short chain APGs such as C4 and/or C6 or mixtures thereof will be suitable with the present invention. As disclosed above, the alkyl polyglycoside is present in the cleaning composition in an amount ranging of from about 0.1% to about 90%, or from about 0.1% to about 70%, or from about 0.1% to about 50%, or from about 0.1% to about 25%, or from about 0.1% to about 10%, or from about 0.1% to about 8.0%, or from about 0.1% to about 7.0%, or from about 0.1% to about 6.0%, or from about 0.1% to about 5.0%, or from about 0.1% to about 4.0%, or from about 0.1% to about 3.0% or from about 0.1% to about 2.0% or from about 0.1% to about 1.0%.

Natural Surfactants

In a most preferred embodiment of the present invention, the surfactants being used in the present invention are natural surfactants. Natural surfactants include but are not limited to, betaines, sarcosinates (i.e. myristoyl sarcosinates, lauroyl sarcosinates, cocoyl sarcosinates), amino propionates (i.e. disodium lauryl b-amino propionate), alkyl polyglucosides, sorbitan esters (i.e. Span® 80, Span® 60, Tween® 80), glycerol monooleate, glycerol monoesterate, emollients, sucrose esters, ester glycol fatty acid, decyl glucoside, lauryl glucoside, caprilic/capric triglycerides and mixtures thereof. Natural surfactants are distinguished from synthetic surfactants which are derived from petrochemicals.

Polyaluminum Compounds

Polyaluminum compounds, includes but are not limited to, polyaluminum chlorides, polyaluminum sulfates, aluminum chlorohydrates, polyaluminum sulfosilicates, polyaluminum silicate chloride, polyaluminum hydroxide chloride silicates, polyaluminum hydroxide chloride silicate sulfates, alum, poly aluminum compounds containing both chloride and sulfate ions, polyaluminum silicate, and mixtures thereof. Polyaluminum compounds may be used in conjunction with colloidal material such as colloidal silica to further enhance its ability to remove dirt and grime from a surface. The present invention can also work with the following compounds as well ammonium aluminum sulfates, potassium aluminum sulfates or other compounds of the general formula $M_2SO_4 \cdot MIII_2(SO4)_3 \cdot 24H2O$, where M is one of the following alkali metals (e.g. potassium, sodium, rubidium, cesium, silver, thallium, and ammonium) and MIII denotes one of the trivalent cations (e.g. aluminum, chromium, iron, manganese, cobalt, titanium).

In one embodiment, the present invention comprises polyaluminum chloride (also known as aluminum chlorohydrate) which is a polymer used as a flocculent. PAC refer to a class of soluble aluminum products in which aluminum chloride has been partly reacted with base. The relative amount of base, compared to the amount of aluminum determines the basicity of the PAC. The chemistry of PAC is often expressed in the following generic formula:

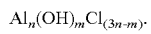

$$Al_n(OH)_m Cl_{(3n-m)}.$$

The actual pH correlates to the formula m/(3n). PAC usually has a low molecular weight, is odorless, colorless and inert. PAC usually consist of inorganic aluminum oxide polymers with very high charge density. The average molecular weight of PAC is between about 1,500 g/mol-2,000 g/mol.

Flocculation is a process when a solute comes out of solution in the form of flakes or floc. The action differs from precipitation in that the solute coming out of solution does so at a concentration generally below its solubility limit in the liquid. Positively charged flocculants attract and stick to many of the suspended water particles. Many of the flocculant cations, under appropriate pH and other conditions, react with water to form insoluble hydroxides which join together to form larger settleable particles or physically traps small particles into the larger floc. Flocculants are used in water treatment processes to improve the sedimentation or filterability of small particles. Generally flocculants are multivalent cations such as aluminium, iron, calcium or magnesium. The most common PAC for water purification is $Al_{12}Cl_{12}(OH)_{24}$. The form of $Al_2Cl(OH)_5$ is used as a deodorant and an antiperspirant. Other modified PAC compounds include polyaluminum hydroxidechloride silicate (PACS) and polyaluminum hydroxidechloride silicate sulfate (PASS).

Suitably, the polyaluminum compound is present in the cleaning composition in an amount ranging from about 0.01% to about 25%, or from about 0.01% to about 20%, or from about 0.01% to about 10.0%, 0.01% to about 5.0%, or from 0.01% to about 5.0%, or from about 0.05% to about 5.0%, or from about 0.05% to about 4.0%, or from about 0.05% to about 3.0%, or from about 0.05% to about 2.0%, or from about 0.01% to about 0.5%, or from about 0.05% to about 1.0%, or from about 0.1% to about 2.0%, or from about 0.1% to about 3.0%, or from about 0.1% to 4.0% or from 0.1% to about 5.0%.

Solvent

The cleaning compositions can contain limited amounts of organic solvents, such as ethanol, sorbitol, glycerol, propylene glycol, and 1,3-propanediol, for example less than 10%, or less than 5%. Sugar alcohols can be suitable for the present invention. Sugar alcohols, include but are not limited to, sorbitol, propanol, glycerol, xilytol, lactitol, maltitol, mannitol, isomalt, erythritol, and mixtures thereof. Monohydric alcohols also can be suitable for the present invention. Monohydric alcohols include, but are not limited to, ethanol, methanol, isopropanol, n-propanol and butanol, t-butanol and mixtures thereof. Polyols are also suitable with the present invention. Polyols include but are not limited to, 1,3-propanediol, 1,3-propanetriol, ethylene glycol and propylene glycol and mixtures thereof. Fatty acid methyl ester can be suitable for the present invention. Fatty acid methyl ester, include but are not limited to, alkylated methyl esters ($\leq$C18), soy-derived fatty acid methyl ester, canola-derived fatty acid methyl ester. Short chain alcohols are also suitable with the present invention. Aloe leaf extract and d-limonine are also suitable solvents for the present invention. Additionally, natural derived triglycerides and lactate ester sorbitol are suitable solvents for the present invention. The compositions preferably contain solvents from natural sources rather than solvents from synthetic petrochemical sources, such as glycol ethers, hydrocarbons, and polyalkylene glycols. While it is favored that natural solvents be used with present invention, the present invention can contain solvents such as $C_{1-6}$ alkanols, other $C_{1-6}$ diols, $C_{1-10}$ alkyl ethers of alkylene glycols, $C_{3-24}$ alkylene glycol ethers, polyalkylene glycols, short chain esters, isoparafinic hydrocarbons, mineral spirits, alkylaromatics, terpenes, terpene derivatives, terpenoids, terpenoid derivatives, formaldehyde, and pyrrolidones. Suitably, the solvent is present in the cleaning composition in an amount ranging from about 0.1 to about 10 weight percent, or 0.1 to 5.0 weight percent, or 0.1 to 4.0 weight percent, or 0.1 to 3.0 weight percent, or 0.1 to 2.0 weight percent, or 0.1 to 1.0 weight percent, or 0.5 to 5.0 weight percent, or 0.5 to 4.0 weight percent, or 0.5 to 3.0 weight percent, or 0.5 to 2.0 weight percent, or 0.5 to 1.0 weight percent.

The Nano-Particle Silica Dispersion

The cleaning compositions may optionally contain nanoparticles of colloidal silica. Nanoparticles, defined as particles with diameters of about 400 nm or less, are technologically significant, since they have novel and useful properties due to the very small dimensions of their particulate constituents. "Non-photoactive" nanoparticles do not use UV or visible light to produce the desired effects. Nanoparticles can have many different particle shapes. Shapes of nanoparticles can include, but are not limited to spherical, parallelepiped-shaped, tube shaped, and disc or plate shaped. Suitably, the colloidal silica is present in the cleaning composition in an amount ranging from about 0.1 to about 5.0 weight percent, 0.1 to about 3.0 weight percent, or about 0.1 to about 2.5 weight percent, or about 0.1 to about 2.0 weight percent, or about 0.1 to about 1.5 weight percent, or about 0.1 to about 1.4 weight percent, or about 0.1 to about 1.3 weight percent, or about 0.1 to about 1.2 weight percent, or about 0.1 to about 1.1 weight percent, or about 0.1 to about 1.0 weight percent, or about 0.1 to about 0.8 weight percent, or about 0.1 to about 0.5 weight percent, or about 0.2 to about 1.0 weight percent, about 0.2 to about 0.8 weight percent.

Nanoparticles with particle sizes ranging from about 1 nm to about 400 nm can be economically produced. Particle size distributions of the nanoparticles may fall anywhere within the range from about 1 nm, or less, to less than about 400 nm, alternatively from about 2 nm to less than about 300 nm, alternatively from about 5 nm to less than about 150 nm, alternatively 1 nm to 100 nm, alternatively 5 nm and 50 nm, alternatively 1 nm and 25 nm, and alternatively 1 nm and 10 nm. Preferred ranges of the colloidal silica further include, but are not limited to, less than 400 nm, less than 350 nm, less than 300 nm, less than 250 nm, less than 200 nm, less than 175 nm, less than 150 nm, less than 125 nm, less than 100 nm, less than 90 nm, less than 80 nm, less than 75 nm, less than 70 nm, less than 60 nm, less than 50 nm, less than 40 nm, less than 30 nm, less than 25 nm, less than 20 nm, less than 10 nm, less than 9 nm, less than 8 nm, less than 7 nm, less than 6 nm, less than 5 nm, less than 4 nm, less than 3 nm, less than 2 nm and less than 1 nm. Commercial colloidal silica suspensions having a primary particle size between 5 to 150 nanometer (nm) and a surface area between 50-800 m.sup.2/g are suitable for use in the present invention. The surface area is generally measured by BET (see DIN 66131; originally described in JACS, Vol. 60, 1938, p. 309 by Brunauer, et al. Colloidal suspensions are generally preferred for ease of handling in preparing the inventive compositions, but these may also be prepared using any available source of colloidal silica according to methods known in the art.

The source of colloidal silica may be selected from silica dioxide, silicon dioxide, crystalline silica, quartz, amorphous fumed silica, food grade silica, flint, hydrophobic fumed silica, treated fumed silica, untreated fumed silica, amorphous fused silica, precipitated amorphous silica, microcrystalline silica, foundry sand, utility sand, fracturing sand, silica sand, silica, flint, glass sand, melting sand, engine sand, blasting sand, traction sand, hydraulic fracturing sands, filter sand, soft silica, condensed silica fume, cristobalite, tridymite, synthetic fused silica, hydrated precipitated silica, colloidal silica, silica dispersion, and silica aerogels. Further, silicas may be selected from the general categories of silicone dioxide ($SiO_2$) described as aerogel, amorphous, colloidal, crystalline, diatomaceous, food grade, fumed, fused, hydrophilic, hydrophobic, novaculite, precipitated, quartz and/or synthetic silica. Amorphous (CAS #7631-86-9), crystalline (CAS # 14808-60-7), and/or mixed type colloidal silica particles may be employed. Generally, amorphous silica forms are preferably employed for applications in which their improved safety characteristics are desirable. Also suitable is amorphous fumed silica, crystalline-free (CAS # 112945-52-5), amorphous hydrated silica and synthetic amorphous silica gel ($SiO.sub.2xH2O$, x=degree of hydration, CAS # 63231-67-4), precipitated silica gel, crystalline-free (CAS # 112926-00-8), amorphous, precipitated silica gel (CAS #7699-41-4), silica hydrate (CAS #10279-57-9), vitreous silica (CAS # 60676-86-0) and crystalline-free silicon dioxide (CAS #7631-86-9).

Suitable amorphous silicas commercially available in the preferred colloidal nanometer size domain include Ludox (available from Dupont), Klebosol (available from Clariant), Bindzil, Nyacol (both available from Akzo Nobel), Levasil (available from Bayer), Koestrosol (available from CWK), and Snowtex (available from Nissan Chemicals). For example, two varying sized colloidal silica products were evaluated, Bindzil 30/360FG (12 nm), 0.075 ppm and Klebosol 35 V 50 (70 nm), 0.10 ppm.

In one embodiment, the surface of the colloidal silica may be modified. Examples of colloidal silica (modified or unmodified) include, but are not limited to, Bindzil® 215 (anionic surface), Bindizil® 15/500 (anionic surface), Bindizil® 30/360 (anionic surface), Bindizil® 830 (anionic surface), Bindizil® 2034 DI (anionic, acid surface), Bindizil® 9950 (anionic surface), Bindizil® 50/80 (anionic surface), Bindizil® DP5110 (aluminum modified surface), Bindizil® 25AT/360 (aluminum modified surface), Bindizil® CAT80 (cationic surface) and Bindizil® CC30 (silane treated surface).

Fragrances

The cleaning compositions may contain natural essential oils or fragrances. The natural essential oils or fragrances may include lemon oil or d-limonine, a citrus-based fragrance or a vinegar-like (i.e. acetic acid) fragrance or mixtures thereof. Lemon oil or d-limonene helps the performance characteristics of the cleaning composition to allow suitable consumer performance with natural ingredients and a minimum of ingredients. Lemon oil and d-limonene compositions which are useful in the invention include mixtures of terpene hydrocarbons obtained from the essence of oranges, e.g., cold-pressed orange terpenes and orange terpene oil phase ex fruit juice, and the mixture of terpene hydrocarbons expressed from lemons and grapefruit. The essential oils may contain minor, non-essential amounts of hydrocarbon carriers. Suitably, fragrances are present in the cleaning composition in an amount ranging from about 0.01 to about 0.50 weight percent, or 0.01 to 0.40 weight percent, or 0.01 to 0.30 weight percent, or 0.01 to 0.25 weight percent, or 0.01 to 0.20 weight percent, or 0.01 to 0.10 weight percent, or 0.05 to 0.40 weight percent, or 0.05 to 0.30 weight percent, or 0.05 to 0.25 weight percent, or 0.05 to 0.20 weight percent, or 0.05 to 0.10 weight percent.

Essential oils include, but are not limited to, those obtained from thyme, lemongrass, citrus, lemons, oranges, anise, clove, aniseed, pine, cinnamon, geranium, roses, mint, lavender, citronella, eucalyptus, peppermint, camphor, sandalwood, rosmarin, vervain, fleagrass, lemongrass, ratanhiae, cedar and mixtures thereof. Preferred essential oils to be used herein are thyme oil, clove oil, cinnamon oil, geranium oil, eucalyptus oil, peppermint oil, mint oil or mixtures thereof.

Actives of essential oils to be used herein include, but are not limited to, thymol (present for example in thyme), eugenol (present for example in cinnamon and clove), menthol (present for example in mint), geraniol (present for example in geranium and rose), verbenone (present for example in vervain), eucalyptol and pinocarvone (present in eucalyptus), cedrol (present for example in cedar), anethol (present for example in anise), carvacrol, hinokitiol, berberine, ferulic acid, cinnamic acid, methyl salicylic acid, methyl salycilate, terpineol and mixtures thereof. Preferred actives of essential oils to be used herein are thymol, eugenol, verbenone, eucalyptol, terpineol, cinnamic acid, methyl salicylic acid, and/or geraniol.

Other essential oils include Anethole 20/21 natural, Aniseed oil china star, Aniseed oil globe brand, Balsam (Peru), Basil oil (India), Black pepper oil, Black pepper oleoresin 40/20, Bois de Rose (Brazil) FOB, Borneol Flakes (China), Camphor oil, Camphor powder synthetic technical, *Canaga* oil (Java), Cardamom oil, *Cassia* oil (China), Cedarwood oil (China) BP, Cinnamon bark oil, Cinnamon leaf oil, *Citronella* oil, Clove bud oil, Clove leaf, Coriander (Russia), Coumarin (China), Cyclamen Aldehyde, Diphenyl oxide, Ethyl vanilin, Eucalyptol, *Eucalyptus* oil, *Eucalyptus citriodora*, Fennel oil, *Geranium* oil, Ginger oil, Ginger oleoresin (India), White grapefruit oil, Guaiacwood oil, Gurjun balsam, Heliotropin, Isobornyl acetate, Isolongifolene, Juniper berry oil, L-methyl acetate, Lavender oil, Lemon oil, Lemongrass oil, Lime oil distilled, Litsea Cubeba oil, Longifolene, Menthol crystals, Methyl cedryl ketone, Methyl chavicol, Methyl salicylate, Musk ambrette, Musk ketone, Musk xylol, Nutmeg oil, Orange oil, Patchouli oil, Peppermint oil, Phenyl ethyl alcohol, Pimento berry oil, Pimento leaf oil, Rosalin, Sandalwood oil, Sandenol, Sage oil, Clary sage, Sassafras oil, Spearmint oil, Spike lavender, Tagetes, Tea tree oil, Vanilin, Vetyver oil (Java), and Wintergreen. Each of these botanical oils is commercially available.

Builders

The cleaning compositions may optionally contain less than 5.0% builder, or even no builder. Suitably, the builder is present in the cleaning composition in an amount ranging from about 0.01 to about 5.0 weight percent, or 0.01 to less than 4.0 weight percent, or 0.01 to 3.0 weight percent, or 0.01 to 2.0 weight percent, or 0.01 to 1.0 weight percent. The builder can be selected from inorganic builders, such as alkali metal carbonate, alkali metal bicarbonate, alkali metal hydroxide, alkali metal silicate and combinations thereof. These builders are often obtained from natural sources.

The cleaning composition can include a builder, which increases the effectiveness of the surfactant. The builder can also function as a softener, a sequestering agent, a buffering agent, or a pH adjusting agent in the cleaning composition. A variety of builders or buffers can be used and they include, but are not limited to, phosphate-silicate compounds, zeolites, alkali metal, ammonium and substituted ammonium polyacetates, trialkali salts of nitrilotriacetic acid, carboxylates, polycarboxylates, carbonates, bicarbonates, polyphosphates, aminopolycarboxylates, polyhydroxy-sulfonates, and starch derivatives. Builders, when used, include, but are not limited to, organic acids, mineral acids, alkali metal and alkaline earth salts of silicate, metasilicate, polysilicate, borate, hydroxide, carbonate, carbamate, phosphate, polyphosphate, pyrophosphates, triphosphates, tetraphosphates, ammonia, hydroxide, monoethanolamine, monopropanolamine, diethanolamine, dipropanolamine, triethanolamine, and 2-amino-2-methylpropanol. Preferred buffering agents for compositions of this invention are nitrogen-containing materials. Some examples are amino acids such as lysine or lower alcohol amines like mono-, di-, and tri-ethanolamine. Other preferred nitrogen-containing buffering agents are tri(hydroxymethyl)amino methane (TRIS), 2-amino-2-ethyl-1,3-propanediol, 2-amino-2-methyl-propanol, 2-amino-2-methyl-1,3-propanol, disodium glutamate, N-methyl diethanolamide, 2-dimethylamino-2-methylpropanol (DMAMP), 1,3-bis(methylamine)-cyclohexane, 1,3-di-amino-propanol N,N'-tetra-methyl-1,3-diamino-2-propanol, N,N-bis(2-hydroxyethyl)glycine (bicine) and N-tris(hydroxymethyl)methyl glycine (tricine). Other suitable buffers include ammonium carbamate, citric acid, and acetic acid. Mixtures of any of the above are also acceptable. Useful inorganic buffers/alkalinity sources include ammonia, the alkali metal carbonates and alkali metal phosphates, e.g., sodium carbonate, sodium polyphosphate. For additional buffers see WO 95/07971, which is incorporated herein by reference. Other preferred pH adjusting agents include sodium or potassium hydroxide. The term silicate is meant to encompass silicate, metasilicate, polysilicate, aluminosilicate and similar compounds.

Chelating Agent

The cleaning composition can optionally contain a chelating agent. Chelants useful herein include the various alkali metal, ammonium and substituted ammonium polyacetates, carboxylates, polycarboxylates and polyhydroxysulfonates. Non-limiting examples of polyacetate and polycarboxylate builders include the sodium, potassium, lithium, ammonium and substituted ammonium salts of ethylenediamine tetraacetic acid, ethylenediamine triacetic acid, ethylenediamine tetrapropionic acid, diethylenetriamine pentaacetic acid, nitrilotriacetic acid, oxydisuccinic acid, iminodisuccinic acid, mellitic acid, polyacrylic acid or polymethacrylic acid and copolymers, benzene polycarboxylic acids, gluconic acid, sulfamic acid, oxalic acid, phosphoric acid, phosphonic acid, organic phosphonic acids, acetic acid, and citric acid. These chelating agents may also exist either partially or totally in the hydrogen ion form, for example, citric acid or disodium dihydrogen ethylenediamine tetraacetate. The substituted ammonium salts include those from methylamine, dimethylamine, butylamine, butylenediamine, propylamine, triethylamine, trimethylamine, monoethanolamine, diethanolamine, triethanolamine, isopropanolamine, and propanolamine. The amount of chelant added should be in the range of 0.01-10%, more preferably 0.1-2%, by weight of the cleaner.

Fatty Acids and Fatty Acid Esters

The cleaning composition can optionally contain fatty acids and/or fatty acid esters. A fatty acid is a carboxylic acid that is often with a long unbranched aliphatic tail (chain), which is saturated or unsaturated. Fatty acids are aliphatic monocarboxylic acids, derived from, or contained in esterified form in an animal or vegetable fat, oil or wax. Natural fatty acids commonly have a chain of 4 to 28 carbons (usually unbranched and even numbered), which may be saturated or unsaturated. Saturated fatty acids do not contain any double bonds or other functional groups along the chain. The term "saturated" refers to hydrogen, in that all carbons (apart from the carboxylic acid [—COOH] group) contain as many hydrogens as possible. In contrast to saturated fatty acids, unsaturated fatty acids contain double bonds. Examples of fatty acids that can be used in the present invention, include but are not limited to, butyric acid, caproic acid, caprylic acid, capric acid, lauric acid, myristic acid, palmitic acid, stearic acid, arachidic acid, behenic acid, lignoceric acid, myristoleic acid, palmitoleic acid, oleic acid, linoleic acid, alpha-linoleic acid, arachidonic acid, eicosapentaenoic acid, erucic acid, docosahexaenoic acid or mixtures thereof. Additionally, polyglycerol fatty acid ester and/or a monoglycerol fatty acid ester may be also be used with the present invention. Polyglycerol fatty acid ester may be obtained by polymerizing glycerol has been esterified with a fatty acid, use can be made of pentaglycerol or decaglycerol monolaurate, pentaglycerol or decaglycerol monostearate, pentaglycerol or decaglycerol monopalmitate, pentaglycerol or decaglycerol monomyristate, or pentaglycerol or decaglycerol monooleate. Examples of monoglycerol fatty acid ester thereof include monoglycerol oleate, monoglycerol laurate, monoglycerolmonostearate, monoglycerol monopalmitate, monoglycerol monomyristate and monoglycerol monooleate. Suitably, fatty acids and fatty acid esters are present in the cleaning composition in an amount ranging from about 0.01 to about 1.0 weight percent, 0.01 to about 0.50 weight percent, or 0.01 to 0.40 weight percent, or 0.01 to 0.30 weight percent, or 0.01 to 0.25 weight percent, or 0.01 to 0.20 weight percent, or 0.01 to 0.10 weight percent, or 0.05 to 0.40 weight percent, or 0.05 to 0.30 weight percent, or 0.04 to 0.25 weight percent, or 0.04 to 0.20 weight percent, or 0.04 to 0.10 weight percent.

Dyes, Colorants, Preservatives Waxes

The cleaning compositions optionally contain dyes, colorants, preservatives, waxes or contain one or more, or none of these components. These dyes, colorants, preservatives and waxes can be natural (occurring in nature or slightly processed from natural materials) or synthetic. Natural preservatives include benzyl alcohol, potassium sorbate and bisabalol; sodium benzoate and 2-phenoxyethanol. Preservatives, when used, include, but are not limited to, mildewstat or bacteriostat, methyl, ethyl and propyl parabens, short chain organic acids (e.g. acetic, lactic and/or glycolic acids), bisguanidine compounds (e.g. Dantagard and/or Glydant) and/or short chain alcohols (e.g. ethanol and/or IPA). The mildewstat or bacteriostat includes, but is not limited to, mildewstats (including non-isothiazolone compounds) including Kathon GC, a 5-chloro-2-methyl-4-isothiazolin-3-one, KATHON ICP, a 2-methyl-4-isothiazolin-3-one, and a blend thereof, and KATHON 886, a 5-chloro-2-methyl-4-isothiazolin-3-one, all available from Rohm and Haas Company; BRONOPOL, a 2-bromo-2-nitropropane 1,3 diol, from Boots Company Ltd., PROXEL CRL, a propyl-p-hydroxybenzoate, from ICI PLC; NIPASOL M, an o-phenyl-phenol, Na$^+$ salt, from Nipa Laboratories Ltd., DOWICIDE A, a 1,2-Benzoisothiazolin-3-one, from Dow Chemical Co., and IRGASAN DP 200, a 2,4,4'-trichloro-2-hydroxydiphenylether, from Ciba-Geigy A.G. Dyes and colorants include synthetic dyes such as Liquitint® Yellow or Blue or natural plant dyes or pigments, such as a natural yellow, orange, red, and/or brown pigment, such as carotenoids, including, for example, beta-carotene and lycopene. Waxes suitable for use in the composition of this invention include, but are not limited to, vegetable waxes such as carnauba, candelilla, and ouricury; mineral waxes such as montan, paraffin, and microcrystalline waxes; animal waxes such as beeswax; and synthetic waxes such as amide waxes and silicone waxes. Other waxes include, but are limited to, castor wax, rice bran wax, sunflower wax, and mixtures thereof. Combinations of two or more of the aforementioned waxes can also be used in the composition of the present invention. Examples of specific waxes or wax emulsions that can be used with the present invention include Plantatex® HCC (by Cognis).

Water

When the composition is an aqueous composition, water can be, along with the solvent, a predominant ingredient. The water should be present at a level of less than 99.9%, more preferably less than about 99%, and most preferably, less than about 98%. Deionized water is preferred. Where the cleaning composition is concentrated, the water may be present in the composition at a concentration of less than about 85 wt. %.

pH

The pH of the cleaning composition is measured directly without dilution. The cleaning compositions can have a pH of 10 or below, 9 or below, or 8 or below, or 6 or below, or 5 or below, or 4 or below, or 3 or below, or from 2 to 10, or from 2 to 8, or from 2 to 6, or from 2 to 4, or from 3 to 8 or from 3 to 6, or from 3 to 5, or from 4 to 10, or from 4 to 8, or from 4 to 6, or from 5 to 8, or from 6 to 8.

Substances Generally Recognized as Safe

Compositions according to the invention may comprise substances generally recognized as safe (GRAS), including essential oils, oleoresins (solvent-free) and natural extractives (including distillates), and synthetic flavoring materials and adjuvants. Compositions may also comprise GRAS materials commonly found in cotton, cotton textiles, paper and paperboard stock dry food packaging materials (referred herein as substrates) that have been found to migrate to dry food and, by inference may migrate into the inventive compositions when these packaging materials are used as substrates for the inventive compositions.

Suitable GRAS materials are listed in the Code of Federal Regulations (CFR) Title 21 of the United States Food and Drug Administration, Department of Health and Human Services, Parts 180.20, 180.40 and 180.50, which are hereby incorporated by reference. These suitable GRAS materials include essential oils, oleoresins (solvent-free), and natural extractives (including distillates). The GRAS materials may be present in the compositions in amounts of up to about 10% by weight, preferably in amounts of 0.01 and 5% by weight.

Preferred GRAS materials include oils and oleoresins (solvent-free) and natural extractives (including distillates) derived from alfalfa, allspice, almond bitter (free from prussic acid), ambergris, ambrette seed, *angelica, angostura* (*cusparia* bark), anise, apricot kernel (persic oil), asafetida, balm (lemon balm), balsam (of Peru), basil, bay leave, bay (myrcia oil), bergamot (bergamot orange), bois de rose (*Aniba rosaeodora* Ducke), cacao, camomile (chamomile) flowers, *cananga, capsicum*, caraway, cardamom seed (cardamon), carob bean, carrot, cascarilla bark, *cassia* bark, Castoreum, celery seed, cheery (wild bark), chervil, cinnamon bark, Civet (zibeth, zibet, zibetum), ceylon (*Cinnamomum zeylanicum* Nees), cinnamon (bark and leaf), *citronella*, citrus peels, clary (clary sage), clover, coca (decocainized), coffee, cognac oil (white and green), cola nut (kola nut), coriander, cumin (cummin), curacao orange peel, *cusparia* bark, dandelion, dog grass (quackgrass, *triticum*), elder flowers, estragole (esdragol, esdragon, estragon, tarragon), fennel (sweet), fenugreek, galanga (galangal), *geranium*, ginger, grapefruit, guava, hickory bark, horehound (hoarhound), hops, horsemint, hyssop, immortelle (*Helichrysum augustifolium* DC), jasmine, juniper (berries), laurel berry and leaf, lavender, lemon, lemon grass, lemon peel, lime, linden flowers, locust bean, lupulin, mace, mandarin (*Citrus reticulata* Blanco), marjoram, mate, menthol (including menthyl acetate), molasses (extract), musk (Tonquin musk), mustard, naringin, neroli (bigarade), nutmeg, onion, orange (bitter, flowers, leaf, flowers, peel), *origanum*, palmarosa, paprika, parsley, peach kernel (persic oil, pepper (black, white), peanut (stearine), peppermint, Peruvian balsam, petitgrain lemon, petitgrain mandarin (or tangerine), *pimenta, pimenta* leaf, pipsissewa leaves, pomegranate, prickly ash bark, quince seed, rose (absolute, attar, buds, flowers, fruit, hip, leaf), rose geranium, rosemary, safron, sage, St. John's bread, savory, *schinus molle* (*Schinus molle* L), sloe berriers, spearmint, spike lavender, tamarind, tangerine, tarragon, tea (*Thea sinensis* L.), thyme, tuberose, turmeric, vanilla, violet (flowers, leaves), wild cherry bark, ylang-ylang and zedoary bark.

Suitable synthetic flavoring substances and adjuvants are listed in the Code of Federal Regulations (CFR) Title 21 of the United States Food and Drug Administration, Department of Health and Human Services, Part 180.60, which is hereby incorporated by reference. These GRAS materials may be present in the compositions in amounts of up to about 1% by weight, preferably in amounts of 0.01 and 0.5% by weight.

Suitable synthetic flavoring substances and adjuvants that are generally recognized as safe for their intended use, include acetaldehyde (ethanal), acetoin (acetyl methylcarbinol), anethole (parapropenyl anisole), benzaldehyde (benzoic aldehyde), n-Butyric acid (butanoic acid), d- or l-carvone (carvol), cinnamaldehyde (cinnamic aldehyde), citral (2,6-dimethyloctadien-2,6-al-8, gera-nial, neral), decanal (N-decylaldehyde, capraldehyde, capric aldehyde, caprinaldehyde, aldehyde C-10), ethyl acetate, ethyl butyrate, 3-Methyl-3-phenyl glycidic acid ethyl ester (ethyl-methyl-phenyl-glycidate, so-called strawberry aldehyde, C-16 aldehyde), ethyl vanillin, geraniol (3,7-dimethyl-2,6 and 3,6-octadien-1-ol), geranyl acetate (geraniol acetate), limonene (d-, l-, and dl-), linalool (linalol, 3,7-dimethyl-1,6-octadien-3-ol), linalyl acetate (bergamol), methyl anthranilate (methyl-2-aminobenzoate), piperonal (3,4-methylenedioxy-benzaldehyde, heliotropin) and vanillin.

Suitable GRAS substances that may be present in the inventive compositions that have been identified as possibly migrating to food from cotton, cotton textiles, paper and paperboard materials used in dry food packaging materials are listed in the Code of Federal Regulations (CFR) Title 21 of the United States Food and Drug Administration, Department of Health and Human Services, Parts 180.70 and 180.90, which are hereby incorporated by reference. The GRAS materials may be present in the compositions either by addition or incidentally owing to migration from the substrates to the compositions employed in the invention, or present owing to both mechanisms. If present, the GRAS materials may be present in the compositions in amounts of up to about 1% by weight.

Suitable GRAS materials that are suitable for use in the invention, identified as originating from either cotton or cotton textile materials used as substrates in the invention, include beef tallow, carboxymethylcellulose, coconut oil (refined), cornstarch, gelatin, lard, lard oil, oleic acid, peanut oil, potato starch, sodium acetate, sodium chloride, sodium silicate, sodium tripolyphosphate, soybean oil (hydrogenated), talc, tallow (hydrogenated), tallow flakes, tapioca starch, tetrasodium pyrophosphate, wheat starch and zinc chloride.

Suitable GRAS materials that are suitable for use in the invention, identified as originating from either paper or paperboard stock materials used as substrates in the invention, include alum (double sulfate of aluminum and ammonium potassium, or sodium), aluminum hydroxide, aluminum oleate, aluminum palmitate, casein, cellulose acetate, cornstarch, diatomaceous earth filler, ethyl cellulose, ethyl vanillin, glycerin, oleic acid, potassium sorbate, silicon dioxides, sodium aluminate, sodium chloride, sodium hexametaphosphate, sodium hydrosulfite, sodium phosphoaluminate, sodium silicate, sodium sorbate, sodium tripolyphosphate, sorbitol, soy protein (isolated), starch (acid modified, pregelatinized and unmodified), talc, vanillin, zinc hydrosulfite and zinc sulfate.

Cleaning Substrate

The cleaning composition may be part of a cleaning substrate. A wide variety of materials can be used as the cleaning substrate. The substrate should have sufficient wet strength, abrasivity, loft and porosity. Examples of suitable substrates include, nonwoven substrates, wovens substrates, hydroentangled substrates, foams and sponges and similar materials which can be used alone or attached to a cleaning implement, such as a floor mop, handle, or a hand held cleaning tool, such as a toilet cleaning device. The terms "nonwoven" or "nonwoven web" means a web having a structure of individual fibers or threads which are interlaid, but not in an identifiable manner as in a knitted web. Nonwoven webs have been formed from many processes, such as, for example, meltblowing processes, spunbonding processes, and bonded carded web processes.

Form and Uses

The present invention may be found in the following non-limiting forms: dilutable, spray, wipe or as a solid absorbent particle or article. The compositions of the present invention may used in the following non-limiting examples: air fabric/refresher, glass cleaner, hard surface cleaner, toilet bowl cleaner, dishwashing detergent, disinfectant/cleaning wipe, fabric softener, carpet cleaner, dye fixative and removal of microorganisms and odor from cat litter. The present invention is directed to composition claims and method of cleaning using the composition claims.

Specific Applications and Benefits

The present invention has many versatile applications in the cleaning, laundry, Glad® and cat litter industries.

Without being bound by theory, the present invention could act as a quat enhancer in wipes to ionicly bound cellulose negative sites so that the quat will more readily available, thereby overall less quat. Consequently, money would be saved by using polyaluminum compositions rather than the conventional wipes. Without being bound by theory, the present invention would allow us to use less pine oil in Pine-Sol® products, thereby saving money. Without being bound by theory, the present invention could be used as a light duty liquid detergent by assisting the wetting of the dish surface and breaking up grease from food on the dish. Without being bound by theory, the present invention could be a toilet bowl cleaner by acting as a soft abrasive and that flocculates stains through agglomeration. Without being bound by theory, the present invention could be a hard surface cleaner that breaks grease and sediment through agglomeration and flocculation. Without being bound by theory, the present invention could be a glass cleaner and reduce spotting from water droplets. Additionally, the present invention could be a substitute for costly colloidal silica in glass cleaners, thereby saving money. Without being bound by theory, the present invention could be an air/fresh refresher by absorbing anionic organic molecules (i.e. cyclodextrin) that contribute to malodor. Additionally, the present invention could remove allergens, dust, smoke etc. through electrostatic interactions. This invention could be applied to the following non-limiting soft surfaces such as carpet, upholstery, bedding, towels, curtains, clothes and air sprayer.

Without being bound by theory, the present invention could be used as dye fixative in laundry products to prevent discoloration of products due to bleeding of colors. Without being bound by theory, the present invention could be used as a fabric softener by coating the fabric with positive charge, thereby reducing the static cling and improving the feel of the fabric. Since polyaluminum compounds are colorless and are inorganic molecules, polyaluminum compounds would not yellow clothes due to degradation upon being heating as organic molecules would.

Without being bound by theory, the present invention can be used for cat litter applications by acting as a natural counteracting malodor compound.

EXAMPLES

The compositions are simple, natural, high performance cleaning formulations with a minimum of essential natural ingredients. Competitive cleaners are either natural and inferior in performance or contain additional ingredients that make them non-natural, such as synthetic components. Preferably, the compositions contain only natural preservatives, dyes, and colorants, if any.

Table I and II illustrate air/fabric refreshers compositions of the present invention. Table III illustrates all-purpose cleaner compositions of the present invention. Table IV illustrates glass cleaner compositions of the present invention. Table V illustrates fabric softener compositions to be used with natural sheet. Table VI illustrates fabric softener compositions in liquid form. Table VII illustrates that a composition containing PACs that was treated on a wipe saw an increase in quat release vs. a composition that did not contain PACs.

TABLE I

| Air/Fabric Refreshner | A | B | C | D | E | F |
|---|---|---|---|---|---|---|
| Polyaluminum Chloride | 0.20 | 0.20 | 0.20 | 0.20 | 0.20 | 0.40 |
| APG(Glucopon ® 425N) | 1.00 | 0.00 | 0.00 | 0.00 | 0.00 | 0.00 |
| APG (Triton ™ CG-110) | 0.00 | 0.00 | 0.04 | 0.00 | 0.00 | 0.00 |
| APG (Glucopon ® 215) | 0.00 | 0.00 | 0.00 | 0.00 | 0.00 | 1.00 |
| Tween ® 80 | 0.00 | 0.00 | 0.00 | 0.05 | 0.10 | 0.00 |
| Fragrance | 0.20 | 0.01 | 0.01 | 0.01 | 0.01 | 0.01 |
| Water | Balance | Balance | Balance | Balance | Balance | Balance |

TABLE II

| Air/Fabric Refreshner | G | H | I | J | K | L |
|---|---|---|---|---|---|---|
| Polyaluminum Chloride | 1.00 | 2.20 | 3.70 | 1.45 | 1.90 | 0.75 |
| APG(Glucopon ® 425N) | 1.00 | 0.00 | 0.00 | 0.00 | 0.00 | 0.00 |
| APG (Triton ™ CG-110) | 0.00 | 0.00 | 0.50 | 0.00 | 0.00 | 0.00 |
| APG (Glucopon ® 215) | 0.00 | 0.50 | 0.00 | 2.50 | 3.00 | 0.00 |
| Tween ® 80 | 0.00 | 0.00 | 0.00 | 0.00 | 0.00 | 0.80 |
| Fragrance | 0.20 | 0.01 | 0.00 | 0.01 | 0.01 | 0.01 |
| Preseravtive | 0.1 | 0.00 | 0.00 | 0.00 | 0.00 | 0.00 |
| Ethanol | 2.00 | 2.50 | 0.00 | 0.00 | 0.00 | 0.00 |
| 1,3 Propandiol | 0.00 | 0.00 | 0.00 | 3.00 | 0.00 | 0.00 |
| Colloidal Silica | 0.5 | 0.35 | 0.00 | 0.00 | 0.00 | 0.00 |
| Dye | 0.00 | 0.00 | 0.10 | 0.00 | 0.00 | 0.00 |
| Water | Balance | Balance | Balance | Balance | Balance | balance |

TABLE III

| All-Purpose Cleaner ("APC") | M | N | O | P |
|---|---|---|---|---|
| Polyaluminum Chloride | 0.80 | 1.20 | 1.65 | 1.90 |
| APG (Glucopon ® 425N) | 0.00 | 3.80 | 2.60 | 1.80 |
| APG (Glucopon ® 215) | 2.60 | 0.00 | 0.00 | 1.20 |
| Ethanol | 3.00 | 4.00 | 3.25 | 2.75 |
| Glycerol | 1.30 | 1.50 | 1.10 | 0.90 |
| Fragrance | 0.50 | 0.25 | 0.75 | 0.60 |
| Preservative | 0.50 | 0.25 | 0.75 | 0.60 |
| Water | Balance | Balance | Balance | Balance |

TABLE IV

| Glass Cleaner ("GC") | Q | R | S | T |
|---|---|---|---|---|
| Polyaluminum Chloride | 0.80 | 1.35 | 1.40 | 0.50 |
| APG(Glucopon ® 425N) | 0.00 | 0.80 | 0.50 | 0.40 |
| APG (Glucopon ® 215) | 0.60 | 0.00 | 0.50 | 0.60 |
| Ethanol | 3.00 | 2.90 | 3.25 | 2.90 |
| Fragrance | 0.50 | 0.75 | 0.25 | 0.45 |
| Preservative | 0.50 | 0.25 | 0.75 | 0.55 |
| Water | Balance | Balance | Balance | Balance |

TABLE V

| Fabric Softener on a Natural Sheet | U | V | W | X |
|---|---|---|---|---|
| Polyaluminum Chloride | 9.00 | 11.00 | 13.00 | 7.00 |
| APG (Glucopon ® 215) | 3.00 | 4.00 | 5.00 | 2.00 |
| Monoglycerol Oleate | 8.00 | 24.00 | 16.00 | 12.00 |
| Stearic Fatty Acid | 21.00 | 11.00 | 16.00 | 12.00 |
| Triglycerides (from a vegetable source) | 22.00 | 24.00 | 18.00 | 26.00 |
| Fragrance | 3.00 | 4.00 | 2.00 | 5.00 |
| Bee's Wax | 34.00 | 32.00 | 30.00 | 36.00 |

TABLE VI

| Fabric Softener- Liquid Form | Y | Z | AA | BB |
|---|---|---|---|---|
| Polyaluminum Chloride | 6.00 | 8.00 | 7.00 | 12.00 |
| Glycerol | 17.00 | 21.00 | 15.00 | 9.00 |
| Wax Emusion* | 6.00 | 7.00 | 4.50 | 11.00 |
| Water | Balance | Balance | Balance | Balance |

*Plantatex ® HCC from Cognis Corporation

TABLE VII

| Material | PPM Quat Released |
|---|---|
| Base Material with no active | 1738 |
| Base Material with 2% Polyaluminum Chlorides | 2615 |

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

We claim:
1. A stable, aqueous cleaning composition comprising:
   a. 0.01% to 20.0% of a polyaluminum compound;
   b. 0.1% to 5.0% of a surfactant selected from the group consisting of nonionic, anionic, cationic, amphoteric, zwitterionic and mixtures thereof; and
   c. a solvent selected from the group consisting of ethanol, isopropanol, sorbitol, glycerol, propylene glycol, 1,3-propanediol, methanol, propanol, butanol, soy-derived fatty acid methyl ester, d-limonene, canola-derived fatty acid methyl ester and mixtures thereof.

2. The composition of claim 1, wherein the polyaluminum compound is selected from the group consisting of polyaluminum chloride, polyaluminum chlorohydrate, and polyaluminum sulfate.

3. The composition of claim 2, wherein the composition further comprises a solvent selected from the group consisting of ethanol, glycerol, and mixtures thereof.

4. The composition of claim 3, wherein the solvent is glycerol.

5. The composition of claim 4, wherein the surfactant is a nonionic surfactant and said nonionic surfactant is an alkyl polyglucoside.

6. The composition of claim 5, wherein the composition is a natural composition wherein said natural composition has
   a) at least 95% of the components of the natural composition are derived from plant and mineral based materials;
   b) the natural composition is biodegradable;
   c) the natural composition is minimally toxic to humans;
   d) the natural composition has a LD50>5000 mg/kg; and
   e) the natural composition does not contain non-plant based ethoxylated surfactants, linear alkylbenzene sulfonates, ether sulfates surfactants or nonylphenol ethoxylate.

7. The composition of claim 6, wherein the composition is an ecofriendly composition, wherein said ecofriendly composition has
   a) at least 99% of the components of the ecofriendly composition are derived from plant and mineral based materials;
   b) the ecofriendly composition is biodegradable;
   c) the ecofriendly composition is minimally toxic to humans;
   d) the ecofriendly composition has a LD50>5000 mg/kg; and
   e) the ecofriendly composition does not contain non-plant based ethoxylated surfactants, linear alkylbenzene sulfonates, ether sulfates surfactants or nonylphenol ethoxylate.

8. The composition of claim 6, wherein the composition is being used as an all-purpose cleaner.

9. The composition of claim 6, wherein the composition is being used as a glass cleaner.

10. A stable, aqueous cleaning composition comprising:
    a. 0.01% to 20.0% of a polyaluminum compound;
    b. 0.1% to 5.0% of a surfactant selected from the group consisting of nonionic, anionic, cationic, amphoteric, zwitterionic and mixtures thereof; and
    c. a fragrance.

11. A natural, hard surface cleaning composition comprising:
    a. 0.01% to 20.0% polyaluminum chloride;
    b. 0.1% to 5.0% of an alkyl polyglucoside; and
    c. a fragrance.

12. The composition of claim 11, wherein the composition further comprises a solvent selected from the group consisting of ethanol, isopropanol, sorbitol, glycerol, propylene glycol, 1,3-propanediol, methanol, butanol, soy-derived fatty acid methyl ester, d-limonene, canola-derived fatty acid methyl ester and mixtures thereof.

13. The composition of claim 12, wherein the solvent is selected from the group consisting of glycerol, sorbitol, 1,3-propanediol and mixtures thereof.

14. The composition of claim 13, wherein the composition is a natural composition, wherein said natural composition has
    a) at least 95% of the components of the natural composition are derived from plant and mineral based materials;
    b) the natural composition is biodegradable;
    c) the natural composition is minimally toxic to humans;
    d) the natural composition has a LD50>5000 mg/kg; and
    e) the natural composition does not contain non-plant based ethoxylated surfactants, linear alkylbenzene sulfonates, ether sulfates surfactants or nonylphenol ethoxylate.

15. The composition of claim 14, wherein composition is an ecofriendly composition, wherein said ecofriendly composition has
    a) at least 99% of the components of the ecofriendly composition are derived from plant and mineral based materials;
    b) the ecofriendly composition is biodegradable;
    c) the ecofriendly composition is minimally toxic to humans;
    d) the ecofriendly composition has a LD50>5000 mg/kg; and
    e) the ecofriendly composition does not contain non-plant based ethoxylated surfactants, linear alkylbenzene sulfonates, ether sulfates surfactants or nonylphenol ethoxylate.

16. A method for cleaning a surface using natural ingredients comprising:
    contacting the surface with a composition, wherein the composition comprises
      a. 0.01 to 20% polyaluminum chloride;
      b. 0.1 to 5% of an alkyl polyglucoside; and
      c. a solvent selected from the group consisting of ethanol, isopropanol, sorbitol, glycerol, propylene glycol, 1,3-propanediol, methanol, butanol, soy-derived fatty acid methyl ester, d-limonene, canola-derived fatty acid methyl ester and mixtures thereof.

17. The method of claim 16, wherein the alkyl polyglucoside is a C8-C10 alkyl polyglucoside.

18. The method of claim 16, wherein the composition further comprises a fragrance.

19. The method of claim 18, wherein the composition is a natural composition, wherein said natural composition has
    a) at least 95% of the components of the composition are derived from plant and mineral based materials;
    b) the composition is biodegradable;
    c) the composition is minimally toxic to humans;
    d) the composition has a LD50>5000 mg/kg; and
    e) the composition does not contain non-plant based ethoxylated surfactants, linear alkylbenzene sulfonates, ether sulfates surfactants or nonylphenol ethoxylate.

20. A stable, aqueous composition comprising:
    a. 0.01% to 20.0% of a polyaluminum compound;
    b. 0.1% to 25.0% of a surfactant selected from the group consisting of nonionic, anionic, cationic, amphoteric, zwitterionic and mixtures thereof; and
    c. a solvent selected from the group consisting of ethanol, isopropanol, sorbitol, glycerol, propylene glycol, 1,3-propanediol, methanol, propanol, butanol, soy-derived fatty acid methyl ester, d-limonene, canola-derived fatty acid methyl ester, glycol ether, isoparafinic hydrocarbon and mixtures thereof.

21. The composition of claim 20, wherein the surfactant is a nonionic surfactant and the nonionic surfactant is an alkyl polyglucoside.

22. The composition of claim 21, wherein the composition further comprises a natural surfactant wherein the natural surfactant is a sorbitan ester.

23. The composition of claim 21, wherein the composition is used as an air refresher or a fabric refresher.

24. The composition of claim 23, wherein the composition is a natural composition, wherein said natural composition has
    a) at least 95% of the components of the natural composition are derived from plant and mineral based materials;
    b) the natural composition is biodegradable;
    c) the natural composition is minimally toxic to humans;
    d) the natural composition has a LD50>5000 mg/kg; and
    e) the natural composition does not contain non-plant based ethoxylated surfactants, linear alkylbenzene sulfonates, ether sulfates surfactants or nonylphenol ethoxylate.

25. The composition of claim 24, wherein the composition is an ecofriendly composition, wherein said ecofriendly composition has
    a) at least 99% of the components of the ecofriendly composition are derived from plant and mineral based materials;
    b) the ecofriendly composition is biodegradable;
    c) the ecofriendly composition is minimally toxic to humans;
    d) the ecofriendly composition has a LD50>5000 mg/kg; and
    e) the ecofriendly composition does not contain non-plant based ethoxylated surfactants, linear alkylbenzene sulfonates, ether sulfates surfactants or nonylphenol ethoxylate.

26. The composition of claim 21, wherein the composition further comprises a component selected from the group consisting of wax, wax emulsion and mixtures thereof.

27. The composition of claim 26, wherein the composition is used as a fabric softener.

28. The composition of claim 27, wherein the composition is a natural composition, wherein said natural composition has
    a) at least 95% of the components of the natural composition are derived from plant and mineral based materials;
    b) the natural composition is biodegradable;
    c) the natural composition is minimally toxic to humans;
    d) the natural composition has a LD50>5000 mg/kg; and
    e) the natural composition does not contain non-plant based ethoxylated surfactants, linear alkylbenzene sulfonates, ether sulfates surfactants or nonylphenol ethoxylate.

29. The composition of claim 28, wherein the composition is an ecofriendly composition, wherein said ecofriendly composition has
    a) at least 99% of the components of the ecofriendly composition are derived from plant and mineral based materials;
    b) the ecofriendly composition is biodegradable;
    c) the ecofriendly composition is minimally toxic to humans;
    d) the ecofriendly composition has a LD50>5000 mg/kg; and
    e) the ecofriendly composition does not contain non-plant based ethoxylated surfactants, linear alkylbenzene sulfonates, ether sulfates surfactants or nonylphenol ethoxylate.

30. A stable, aqueous air or fabric refresher composition comprising:
    a. 0.01% to 20.0% of a polyaluminum compound;
    b. 0.1% to 10.0% of an alkyl polyglucoside;
    c. a solvent selected from the group consisting of ethanol, isopropanol, sorbitol, glycerol, propylene glycol, 1,3-propanediol, methanol, propanol, butanol, soy-derived fatty acid methyl ester, d-limonene, canola-derived fatty acid methyl ester, glycol ether, isoparafinic hydrocarbon and mixtures thereof;
    d. a fragrance; and
    e. pH 2 to 10.

31. A stable, aqueous fabric softener composition comprising:
    a. 0.01% to 20.0% of a polyaluminum compound;
    b. 0.1% to 10.0% of an alkyl polyglucoside;
    c. a solvent selected from the group consisting of ethanol, isopropanol, sorbitol, glycerol, propylene glycol, 1,3-propanediol, methanol, propanol, butanol, soy-derived fatty acid methyl ester, d-limonene, canola-derived fatty acid methyl ester, glycol ether, isoparafinic hydrocarbon and mixtures thereof;
    d. a component selected from the group consisting of a wax, wax emulsion and mixtures thereof; and
    e. pH 2 to 10.

* * * * *